United States Patent [19]

Thomas et al.

[11] Patent Number: 4,878,116
[45] Date of Patent: Oct. 31, 1989

[54] VECTOR LOCK-IN IMAGING SYSTEM

[75] Inventors: Robert L. Thomas, Huntington Woods; Pao-Kuang Kuo, Troy; Lawrence D. Favro, Huntington Woods, all of Mich.

[73] Assignee: Wayne State University, Detroit, Mich.

[21] Appl. No.: 202,185

[22] Filed: Jun. 2, 1988

[51] Int. Cl.[4] .......................... H04N 5/14; H04N 5/30
[52] U.S. Cl. .................................... 358/160; 358/110; 358/111; 358/113
[58] Field of Search ............ 358/160, 111, 110, 21 R, 358/113, 36, 167

[56] References Cited

U.S. PATENT DOCUMENTS 4,409,615 10/1983 McMann, Jr. et al. ............. 358/111
4,458,267 7/1984 Dolazza .............................. 358/111
4,636,850 1/1987 Stewart ................................ 358/111

Primary Examiner—Edward L. Coles, Sr.
Assistant Examiner—Michael D. Parker
Attorney, Agent, or Firm—Reising, Ethington, Barnard, Perry & Milton

[57] ABSTRACT

The assembly (10) is a real-time imaging device for detecting radiation from an object field which is periodic in time. A video camera (14) detects emitted and reflected radiation from the object field (12) and produces a video signal comprising a series of pixels representing a frame of the image. The video signal is digitized (18) and received by a processor (16). The processor (16) averages the successive frames as in-phase images and quadrature images based on the periodicity of the object field to eliminate unsynchronous noise from the image and to display an image synchronous with the periodicity.

27 Claims, 6 Drawing Sheets

VECTOR LOCK-IN IMAGING SYSTEM

TECHNICAL FIELD

The invention relates to a real-time imaging system operating in synchronism with an object field which is periodic in time wherein unsynchronous background noise is filtered leaving only relevant, synchronous time varying information in the image.

BACKGROUND OF THE INVENTION

Objects in conventional photography or detection reflect and may emit radiation of their own, and such detection of radiation includes all reflected and emitted radiation. Lock-in detection has been used with detectors wherein an object is externally stimulated and the lock-in detector detects only information of the image signal in synchronism with the reference stimulation signal.

In infrared (IR) or thermal imaging all objects emit thermal radiation of their own in addition to reflecting radiation of other objects. What is recorded in a thermograph is always a mixture of emitted and reflected radiation, some of which even comes from components of the camera, including lenses and their supporting structures. This problem is particularly severe in the 8-12 micrometer range, because it corresponds to the peak of black body radiation at room temperature. It is the same range of wavelength that is most relevant for nondestructive evaluation. In conventional scanned thermal wave imaging applications, this problem is overcome by the use of a lock-in analyzer synchronized to the source of the thermal waves. Without the lock-in technique, the IR video camera is capable of observing only very slow thermal phenomena. This limitation offsets the main advantage of the IR video camera, namely its high data-acquisition rate.

U.S. Pat. No. 4,652,757 issued Mar. 24, 1987 granted in the name of Carver discloses an infrared detector detecting a reflected probe beam that is modulated at the pump beam frequency produced by the pump laser. The lock-in amplifier allows the detector to process only the modulation frequency of the probe beam. The detected portion is only that which is modulated at the frequency of the pump beam. This is conventional analysis of a single signal with a commercially available lock-in amplifier.

U.S. Pat. No. 4,589,783 issued May 20, 1986 in the name of Thomas et al. discloses a thermal wave imaging system. A first laser beam heats the object and a second probe beam is deflected by the heated air above the object and is detected by a device mounted adjacent to the object and stored in an image memory under the control of central processor. This system also uses a single lock-in amplifier similar in fashion to that described with reference to the Carver patent.

The prior art only discloses receiving a single signal and using a lock-in amplifier to detect only the synchronous image. In general, the IR video camera is capable of observing only very slow thermal phenomena, despite the fact that the intrinsic band width of the camera is very broad. Additionally, without lock-in amplification all unsynchronous noise will be detected and displayed.

SUMMARY OF THE INVENTION AND ADVANTAGES

The invention is an imaging assembly for producing images synchronous with the periodicity of an object field and a method of producing the same. The assembly includes reference means for producing a reference signal representing the periodicity of an object field, and camera means for detecting radiation from the object field producing a video signal of the image comprising a series of pixels representing a frame of the image of the object field and for producing a timing signal for each of the pixels of the frame. Also included is processor means for receiving the frame of the video signal and storing the frame synchronously with the reference signal and for averaging the stored frame with subsequently received frames having the pixels synchronous with the reference signal producing an image signal. Display means receives the image signal and displays the averaged image.

The assembly provides an imaging system for an object field with a temporal periodicity producing a reference signal wherein information of each pixel of the frame of an image is handled in the manner f a lock-in analyzer; only portions of the image which are synchronized with the reference signal are averaged and displayed. Therefore, unsynchronized background radiation is rejected and the signal to noise ratio is enhanced.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
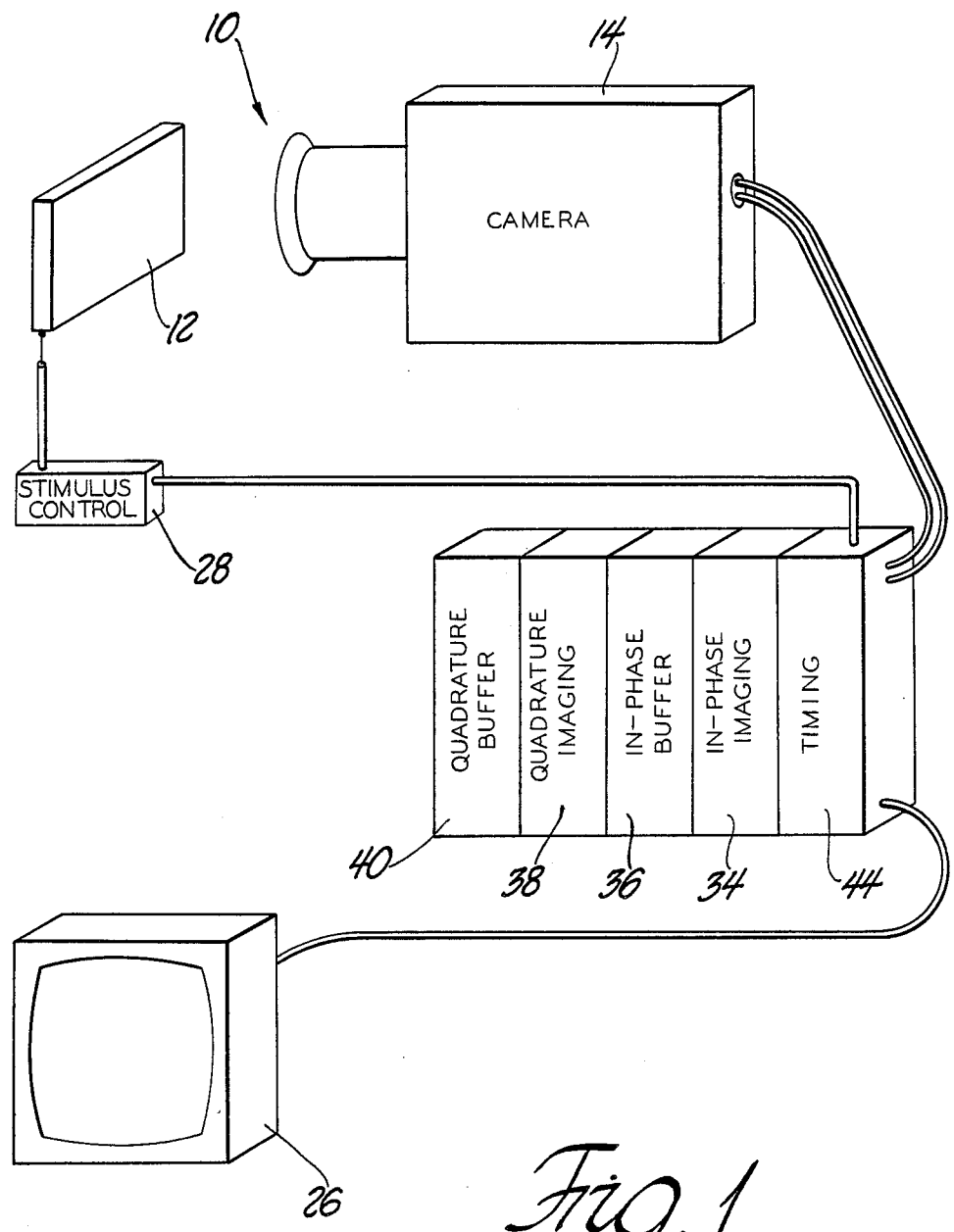
FIG. 1 is a perspective view of the subject invention.

An imaging assembly 10 for producing images in synchronism with the periodicity of an object field 12 is generally shown at 10 in FIG. 1. Images are produced of the synchronous component of the object field 12. The assembly 10 requires that the portion of interest of the video signal be periodic, or quasi-periodic, and be capable of serving as a reference frequency for synchronization of the assembly 10. In some cases this periodicity may occur naturally, e.g., blood flow driven at the pulse rate of the heart. In other cases, the periodicity may be induced by an external stimulus, e.g., a modulated laser beam, flash lamp, or modulated electric or magnetic field, or modulated electric currents. The assembly 10 achieves, in parallel, and in real time, the effect of lock-in signal averaging for each of the pixels produced by the video camera. An advantage over prior art imaging systems is the resultant improvement in sensitivity while not relinquishing the advantage of real-time imaging offered by prior art assemblies.

The object field 12 to be imaged may be comprised of any field which is capable of generating its own periodic radiation or generating radiation in response to being externally, periodically stimulated. Examples of such applicability include: synchronous thermal wave imaging for nondestructive evaluation in manufacturing processes; medical thermographs which detect the minute skin temperature change induced by blood flow which is synchronous with the heart beat, useful in the detection of near superficial cancerous growth and condition of blood circulation in different parts of the body; synchronous detection of fluorescence resulting from modulated ultraviolet light used as an external stimulus useful in crime prevention, examination of objects of art, etc.

The assembly 10 includes camera means 14 for detecting radiation from an object field 12 providing video and sync timing information which may be in the form of separate signals or may be in the form of composite video signals in which the video and sync timing signals are combined into one composite video signal. These signals comprise electrically the image of the object field 12 and include timing and phase information of each frame of the image. The video signal comprises passive and active radiation. The passive radiation is that which occurs naturally, such as reflected radiation or the object's own emitted radiation. The active radiation is that resulting from external periodic irradiation of the object field 12 or that radiation internally generated by the object field 12. A conventional television camera or infrared camera 14, or other camera may be used to obtain the image in the form of pixels accumulated to produce a frame. In this embodiment, the camera means 14 produces a composite video signal wherein each pixel of a frame of the image is serially transmitted, and therefore the frames are serially transmitted. The composite video signal is a continuous signal interrupted after each frame. The camera means 14 repeatedly forms an image of the object field 12 and continuously produces the composite video signal comprising the pixels forming the image. The pixels forming one image constitute a frame and the composite video signal transmits images, frame after frame. The frame is comprised of lines of pixels. In effect, the assembly 10 increases the number of channels to that of the number of pixels in the video image, namely 262,144 in the preferred embodiment. Typically, 25 or 30 frames/second are obtained by the camera 14. The timing and phase information enables the processor means 16 to derive detailed information about the timing of each pixel of the image. This provides the mechanism for acquiring digital images in synchronism with the periodicity of the object field 12, as subsequently described.

Figure 2:
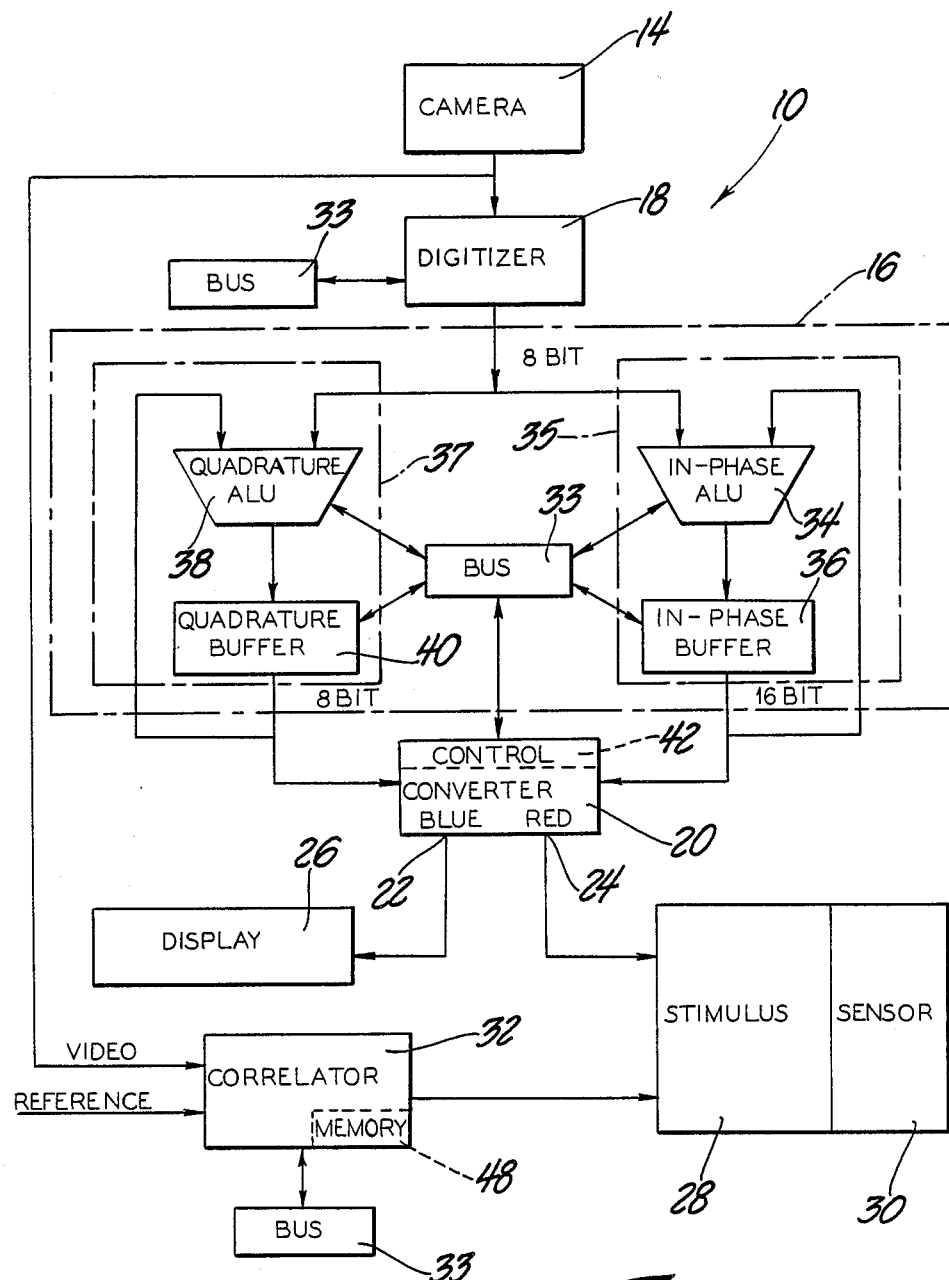
FIG. 2 is a block diagram of the subject invention.

As generally shown in FIG. 2, the assembly 10 includes a processor means 16 for receiving the video signal and accumulating or reproducing a frame of the image and subsequently averaging the frame with subsequent frames producing an image signal representative of the averaged frame image synchronous with the periodicity of the object field 12. In this embodiment, the processor means 16 obtains a sync timing signal from the composite video signal produced by the camera means 14 representing time and phase information of each frame and the reference signal representing the periodic external stimulation or internally produced periodicity of the object field 12, as will be described subsequently. Based upon the phase relationship between the timing signal and reference signal, the processor means 16 obtains the in-phase image and quadrature image of the object field 12, in a fashion similar to that of a vector lock-in detector. The processor means 16 may be comprised of off-the-shelf components, as will be described subsequently. The processor means 16 acts as the lock-in device for a frame of the entire image.

The assembly 10 includes digitizer means 18 for converting the composite video signal into a digital video signal. The digitizer means 18 receives and converts the analog video signal from the camera means 14 into the digital video signal wherein the coding represents the intensity of each pixel of the image. In the preferred embodiment, the digital video signal is comprised of an eight bit binary code signal per pixel. In other words, the digitizer means converts the serially received analog pixel information and converts each pixel of information into the eight bit binary code.

The assembly 10 includes converter means 20 for receiving the image signal from the processor means 16 to convert it into an analog display signal for the display means 26, and for receiving the synchronizing signal from the bus means 33 to produce a synchronous control signal. In the preferred embodiment, the converter means 20 provides Red, Green, Blue (RGB) color outputs. The Blue color output 22 produces the analog display signal and the Red color output 24 produces the synchronous control signal.

The processor means 16 includes display means 26 for receiving the analog display signal from the Blue output and for displaying the in-phase image or quadrature image of the object field 12. Any display or terminal capable of graphics display may be used.

The subject invention utilizes an object field 12 which is externally periodically stimulated at the reference frequency, or an object field 12 which internally produces periodicity of the reference signal. Stimulus control means 28 is included for externally stimulating the object field 12 at the reference signal frequency. The stimulus control means 28 may provide the periodicity by modulated laser beam, flash lamp, modulated electric currents, or any other means which will produce the requisite periodic or quasi-periodic radiation. In the preferred embodiment, the IR camera 14 has a pixel rate of 4 MHz which sets the maximum intrinsic limit of the reference or lock-in frequency at about 1 MHz. Alternatively, if using a single phase accumulating system, it is possible to have the frequency at 2 MHz. If the periodicity occurs naturally in the object field 12, such as heart rate, the stimulus control means 28 is unnecessary. Instead, a sensor means 30 senses the periodicity of the object field 12 to produce the reference signal for the processor means 16.

The assembly 10 includes correlating means 32 for receiving the composite video signal to obtain the sync timing signal and for receiving the reference signal to produce command signals to control the processor means 16 and digitizer means 18, and the stimulus control means 28 when necessary. The digitizer means 18 synchronously generates a pixel timing signal based on the sync timing signal and transmits the same to the processor means 16 in a daisy chain for the timing of operations on the pixels. The correlating means 32 also includes bus means 33 for transmitting the command signals to the processor means 16 between frames. The processor means 16 receives commands off the bus means 33 between the sequential frames of the image. When an external stimulus is used, the reference frequency is sent to the correlating means 32 and the sync timing signal is obtained which is further transmitted to the stimulus control means 28 for the periodic stimulation of the object field 12. When the periodic signal is internal to the object field 12, or in other words external stimulation is unnecessary, the sensor means 30 senses the periodicity of the object field 12 and produces the reference signal transmitted to the correlating means 32. The correlating means 32 compares the reference signal and the sync timing signal to establish the phase relationships and determine the function to be undertaken by the processor means 16. As will be subsequently described, the averaging of the frames of data is performed by multiplication and accumulation operations depending on the phase relationships.

The sync timing signal and reference signal for synchronization are managed by the correlating means 32, which communicates with the processor means 16 by the bus means 33, which may be a high speed communication bus, e.g., VME bus. This provides the mechanism for acquiring digital images in synchronism with the periodicity of the object field 12. In the preferred embodiment, the sync timing signal obtained from the camera means 14 received by the correlating means 32 controls the frequency and phase of the reference signal for the stimulus control means 28.

The lock-in detection of the processor means 16 is carried out in two channels of the processor means 16 offset by a quarter of the period of the reference signal, i.e., 90 phase difference. The first channel 35 handles the in-phase information and the second channel 37 handles the quadrature information. This is accomplished by merging the digital video signal with the sine and cosine functions of the phase of the reference signal frequency, and accumulating the results in a buffer of the processor means 16. The sine and cosine functions of the reference signal may be approximated by square waves of the same phase relationship.

The in-phase channel 35 includes in-phase imaging means 34 to process frames of images in-phase with the reference signal. The in-phase channel 35 also includes in-phase buffer means 36 for storing the averaged in-phase image portion. The quadrature channel 37 includes quadrature imaging means 38 to produce the quadrature images of the periodic signal. Quadrature buffer means 40 stores the averaged quadrature images. In the preferred embodiment, the in-phase and quadrature image buffers are each $512 \times 512 \times 16$ bits.

When a predetermined number of frames have been accumulated by the processor means 16, the results are normalized and displayed by the display means 26 as in-phase and quadrature images, analogous to the way a vector analyzer produces in-phase and quadrature components by accumulating a single signal for a period of time. The advantage of parallel processing thereby gained is approximately a quarter of a million.

The converter means 20 includes display control means 42 for handling post-processing: the phase adjustment, feature enhancement, pseudo-color and gray scale image display.

The preferred embodiment of the imaging assembly 10 will be hereinafter described. It is to be understood that the invention is not limited to the specific application of IR imaging, but the embodiment is an example of the assembly's capabilities.

The preferred embodiment of the processor means 16 utilizes periodic heating for the external stimulus of the object field 12. The camera means 14 is a commercial IR camera, such as Inframetrics IR-600. The digitizing means digitizes the video signal at 10 MHz into a byte or 8-bit digitized video signal to be processed by the processor means 16.

Figure 3:
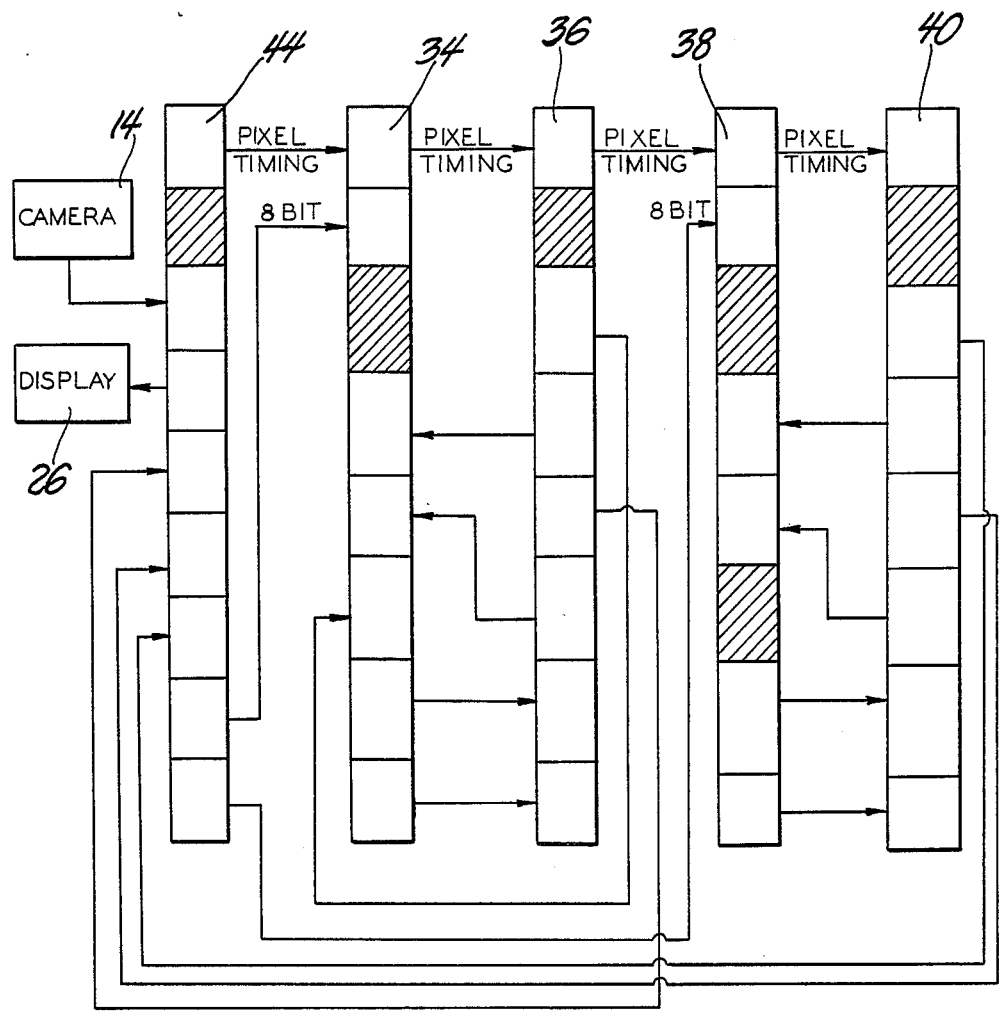
FIG. 3 is schematic diagram of the processor means.
Figure 4A:
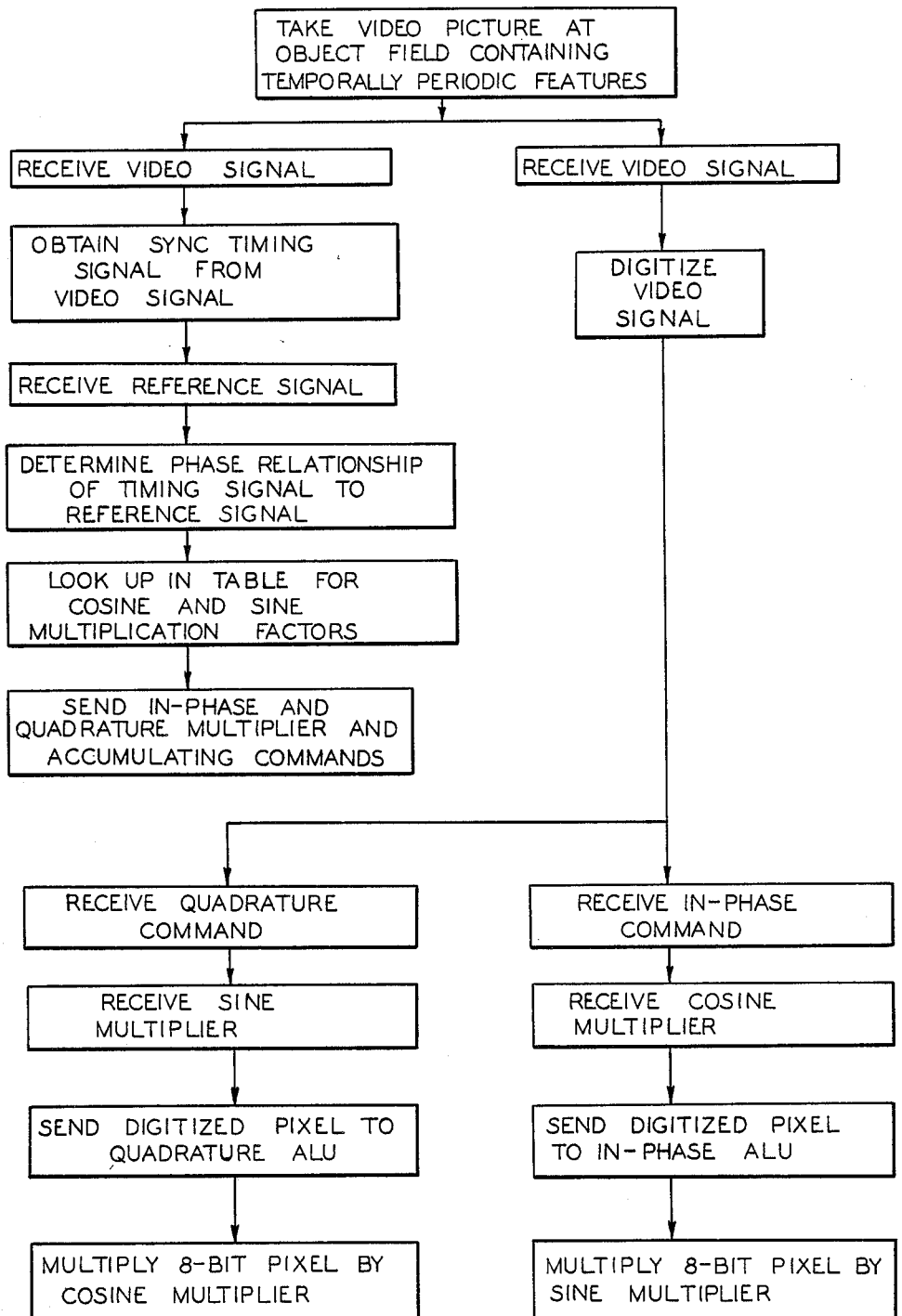
FIG. 4a–b is a flow chart of the subject invention.
Figure 4B:
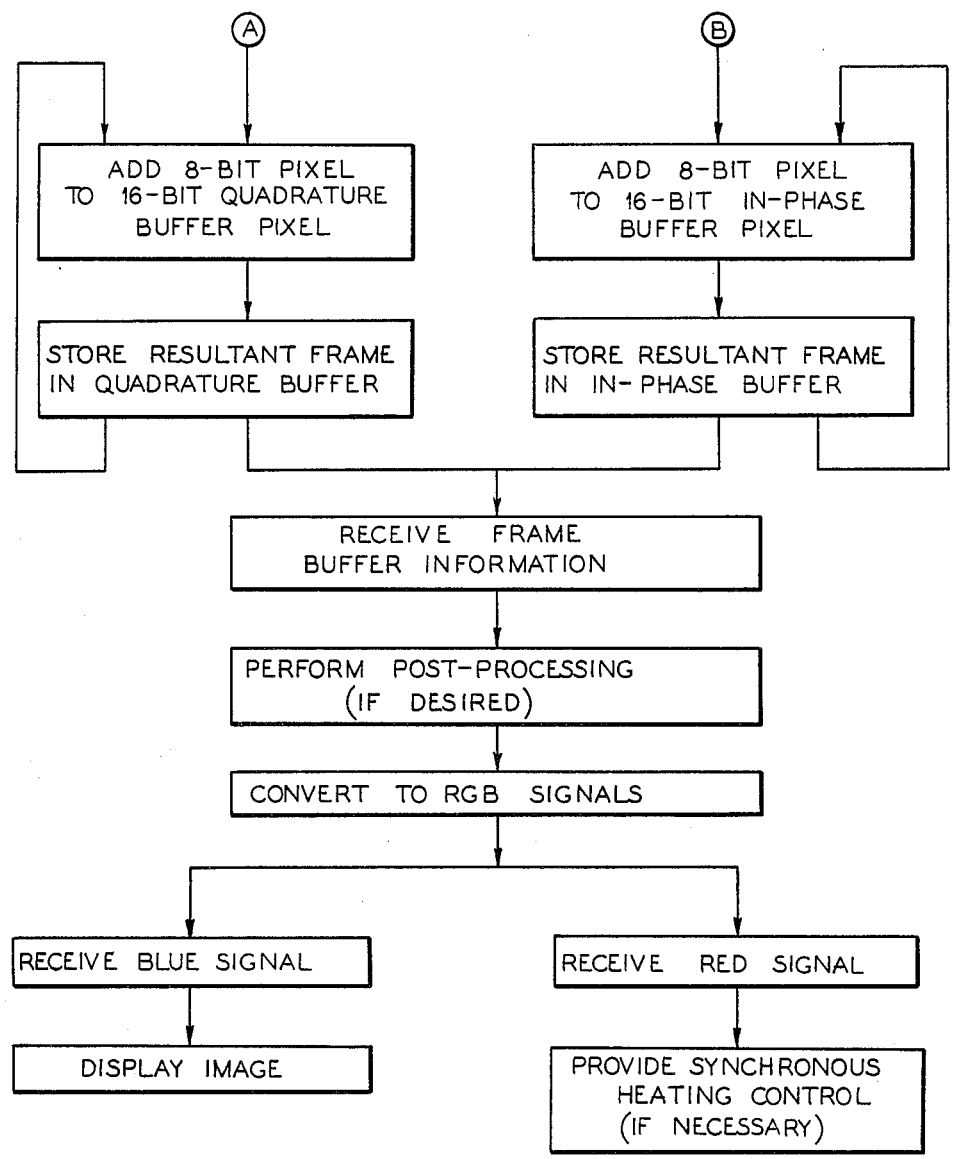
Figure 5:
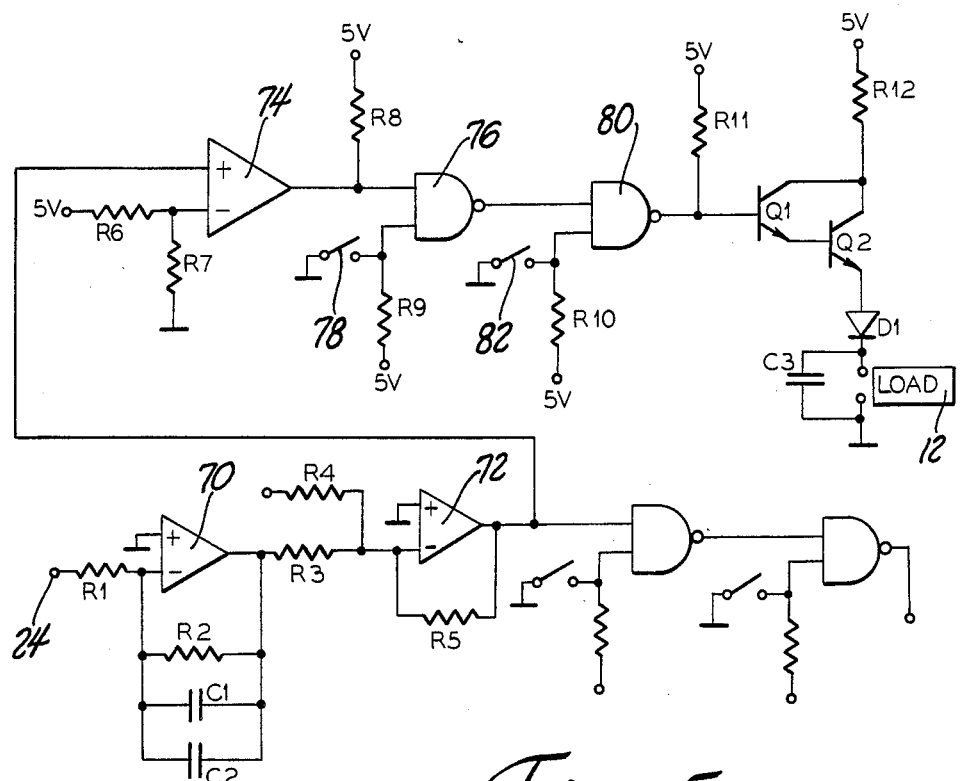
FIG. 5 is a schematic diagram of the stimulus control means.

As indicated in FIG. 3, the digitizer means 18 and converter means 20 reside on a board 44 and the processor means 16 consists of four boards 34, 36, 38, 40 residing on the bus means 33. The boards 44, 34, 36, 38, 40 are manufactured by Datacube, Inc. The display means 26 and correlating means 32 are implemented by the Sun 3/160° C. Color Workstation. The pixel timing signals are sent from board 44 to all the boards 34, 36, 38, 40 on a sixteen (16) conductor flat cable in a daisy chain. The functions of the boards 44, 34, 36, 38, 40 are implemented by software which follows the flow chart in FIG. 4a–b. The four boards 34, 36, 38, 40 are divided into two groups for the in-phase channel 35 and quadrature channel 37 comprising the in-phase imaging means 34 and in-phase buffer means 36 and the quadrature imaging means 38 and quadrature buffer means 40. The in-phase imaging means 34 and the quadrature imaging means 38 perform the functions of multiplying and accumulating the digitized video images in the correct sequence according to the phase information they receive from the bus means 33. The in-phase and quadrature imaging means 34,38 may be implemented by ALUs (arithmetic log units). During each frame, a sixteen bit video data stream is read from the in-phase buffer means 36 and quadrature buffer means 40 and is merged with the eight bit data from the digitizer means 18 in their respective imaging means 34, 38 using the multiply and accumulate operation.

The in-phase imaging means 34 processes the in-phase portion of the video data and stores it in the in-phase buffer means 36, while the quadrature imaging means 38 processes the quadrature portion of the video data and stores it in its quadrature buffer means 40. The in-phase 34 and quadrature 38 imaging means accumulate the digitized video signal in the in-phase 36 and quadrature 40 buffer means 40. In this embodiment, each line is handled as being in the same phase relationship. In other words, each pixel of one line received is assumed to be of the same phase relationship such that the entire line will be handled in the same manner, i.e., each pixel of the line is multiplied by the same sine or cosine values and accumulated in the buffer means 36,40. As previously stated, the correlating means 32 sends commands to the imaging means 34, 38 between successive frames. Of each line the corresponding sine and cosine values are fetched from a look-up table in accordance to the phase of the line relative to the reference signal. The values of the table may be calculated each time when necessary, but for purposes of speed it has been found desirable to store all the values in memory 48 of the correlating means 32. The sine and cosine values are then used as multipliers in the multiply and accumulate operation. Thus, the upper limit of the reference signal in this embodiment is one quarter of the line rate, e.g., 4 KHz. By using the look-up table on a pixel-by-pixel basis, this upper limit can be extended to one quarter of the pixel rate, e.g., 1 MHz. The look-up table and the number of frames to be averaged are prepared in advance by the correlating means 32. When the line look-up table is used, the error introduced by treating the entire line as having the same phase can be corrected during post processing. Alternatively, the phase information and multiply and accumulation commands may be implemented on a frame by frame basis, but will slow the speed of the assembly 10.

The following is an example of a multiplier look-up table for a 90 Hz frequency video lock image acquisition system for a camera using the RS-170 Video Standard. It is assumed that the phase of the reference signal is synchronized and in phase with the frame rate of the camera. According to the RS-170 Standard, there are 525 lines in a frame. The first five lines are listed below. The table includes 526 entries to take into account the fact that the first and last lines are each half-lines. The phases listed are the beginning phases of each line. The beginning of the frame (phase=0 degrees) occurs at the middle of the first line; hence the phase of the first line is negative. The increment of phase between successive lines is approximately 2.057 degrees. If the reference signal and the frame rate of the signal are not in phase, a constant phase correction is added to each of the phase values before the sine and cosine values are calculated and stored in the table.

| Line No. | Phase (Deg.) | Cosine (in-phase) | Sine (quadrature) |
|---|---|---|---|
| 1 | −1.02857 | 0.99984 | −0.17951 |
| 2 | 1.02857 | 0.99984 | 0.01795 |
| 3 | 3.08571 | 0.99855 | 0.05383 |
| 4 | 5.14286 | 0.99597 | 0.08964 |
| 5 | 7.20000 | 0.99212 | 0.12533 |
| . | . | . | . |
| . | . | . | . |
| . | . | . | . |

The in-phase and quadrature image buffers are 16-bit image buffers. Since 16-bit image buffers are used for 8-bit image data, the apparent limit to the accumulation process is 256 frames without overflow. However, because the multiplication factors are alternately positive and negative, the no overflow condition can continue for many more than 256 frames.

The converter means 20 receives the image signal and converts it into the analog RGB output for the display means 26. The digital monochrome data are converted into analog video data and sent out via the RGB Blue output terminal. The display means 26 displays the in-phase or quadrature images from the in-phase or quadrature buffer means 36,40, respectively. After a predetermined numbers of frames are accumulated in the buffers 36,40, the process is stopped and the resulting in-phase and quadrature images can be displayed.

Synchronous heating control signals are provided by the converter means 20 via its Red color output terminal. The stimulus control means 28 receives the Red output by a limiting resistor R1 which is connected to a first operational amplifier 70 at its inverting input. The non-inverting input of the op-amp 70 is connected to ground. The op-amp 70 includes a feedback circuit connected between the inverting input and output and includes a resistor R2 in parallel with a capacitor C1 and in parallel with a second capacitor C2. The output of the op-amp 70 is connected through resistor R3 to the inverting input of a second op-amp 72. A resistor R4 is connected to a 5 volt power and to the inverting input, and the noninverting input of op-amp 72 is connected to ground. A feedback resistor R5 is connected between the inverting input and output. The output of op-amp 72 is sent to the noninverting input of trigger op-amp 74 having its inverting input connected to a voltage divider comprising resistor R6 connected to power and resistor R7 connected to ground. The output of op-amp 74 is connected to a first input of NAND gate 76 which is also connected through resistor R8 to power. The second input of the NAND gate 76 is connected through resistor R9 to power and through a switch 78 to ground. The output of the NAND gate 76 is connected through a first input of NAND gate 80 whose second input is connected through a switch 82 to ground and through resistor R10 to power. The output drives a transistor switch and is connected through resistor R11 to power. The transistor switch comprises a first transistor Q1 with its base connected to the output of the NAND gate 80 and it collector connected via resistor R12 to power. The emitter of transistor Q1 drives the base of transistor Q2 whose collector is also connected to resistor R12 and whose emitter is connected to a diode D1 to the load or object field 12. A capacitor C3 is connected across the load 12.

The invention also includes a method for producing an image of the synchronous component of an object field. The method includes the steps of producing a reference signal representing the periodicity of the object field, detecting radiation from the object field to produce the video signal of the image comprising a series of pixels representing a frame, producing a sync timing signal for each frame based on the video signal, processing the video signal and storing the frame and averaging the stored frame with subsequent frames, and displaying the averaged image. The method further includes digitizing the video signal into a digital video signal for the processing, and receiving the image signal from the processing and converting it into a display signal. Also included are the steps of receiving the sync timing signal, reference signal, and producing synchronizing signals for external stimulation of the object field, and sending multiply and accumulate commands prior to the processing of a subsequent frame based on the relation of the sync timing signal to the reference signal, providing a multiplier factor by looking up the phase relationship in a table. The processing further includes averaging successive frames of the object field in-phase with the reference signal and averaging successive frames of the object field 90 degrees out of phase with the reference signal. The in-phase averaging includes storing the averaged in-phase image frame and receiving the multiply and accumulate command signal and digital video signal and averaged stored in-phase image. The method further includes one of stimulating the object field at the reference signal, and sensing the internal periodicity of the object field to produce the reference signal.

Therefore, the subject invention provides a video camera combined with a video image processor to simulate a large number of lock-in analyzers when the object is illuminated or stimulated with the signal synchronized with the reference signal of the lock-in detection. Information in each pixel of an image is handled as if it were being processed simultaneously by its own lock-in analyzer, in synchronism with the periodic portion of the image.

Figure 6A:
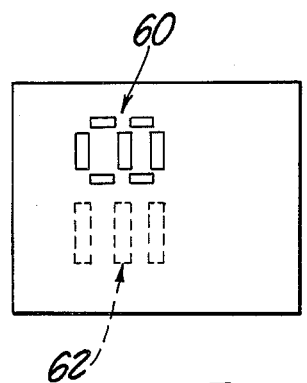
FIG. 6a–b illustrates an application of the subject invention.
Figure 6B:
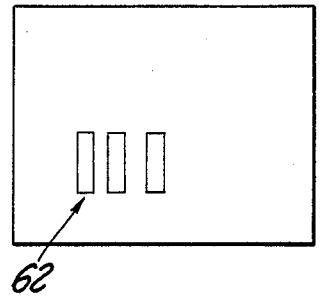

As an example, FIG. 6a shows a video picture of a circuit board containing an LED (light emitting diode) display lamp 60 with all its segments turned on by a dc current. Just below is another LED 62, three of whose segments are energized by a weaker current modulated by the synchronizing signal at the reference signal frequency. FIG. 6b shows the results of the in-phase image after just two cycles of accumulation. One sees that the only discernible features are the modulated LED segments 62, all other features having been eliminated by lock-in detection. Increasing the number of cycles of averaging decreases the background noise but keeps the magnitude of the modulated signal the same. The simultaneous acquisition of both the in-phase and the quadrature images is of importance because it makes possible the reconstruction of the image of any other required phase from stored image data. Such information can be very useful in providing characteristic signatures of different types of subsurface defects.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An imaging assembly for producing images synchronous with the periodicity of an object field (12), said assembly (10) comprising; reference means for producing a reference signal representing the periodicity of an object field (12), camera means (14) for detecting radiation from the object field (12) producing a video signal of the image comprising a series of pixels representing a frame of the image of the object field (12) and for producing a timing signal for each of said pixels of said frame, processor means (16) for receiving said frame of said video signal and storing said frame in synchronism with said reference signal and for averaging said stored frame with subsequently received frames having said pixels synchronous with said reference signal producing an image signal, and display means (26) for receiving said image signal and displaying the averaged image.

2. An assembly as set forth in claim further characterized by including converter means (20) for receiving said image signal and converting it into a display signal to control said display means (26).

3. An assembly as set forth in claim 2 further characterized by said processor means (16) including digitizer means (18) for converting said video signal into a digital video signal for said processor means (16).

4. An assembly as set forth in claim 3 further characterized by including correlating means (32) for receiving said video signal to produce said timing signal and for receiving said reference signal to produce synchronizing signals and to transmit multiply and accumulate commands to said processor means (16) for the averaging.

5. An assembly as set forth in claim 4 further characterized by said correlating means (32) including memory means (48) for storing a look-up table containing by phase relationship of said timing signal to said reference signal a cosine multiplier factor for each relationship, said multiply command including said multiplier factor for each of said pixels.

6. An assembly as set forth in claim 5 further characterized by. said processor means (16) including bus means (33) for transmitting said synchronizing signal to said processor means (16) and said converter means (20) and for transmitting said multiply and accumulate commands to said processor means (16).

7. An assembly as set forth in claim 6 further characterized by said processor means (16) including in-phase channel means for averaging successive frames of said object field (12) in-phase with said reference signal.

8. An assembly as set forth in claim 7 further characterized by said processor means (16) including in-phase buffer means (36) for storing the averaged in-phase image frame.

9. An assembly as set forth in claim 8 further characterized by said processor means (16) including in-phase imaging means (34) for receiving said multiply command from said correlating means (32) and said digital video signal and said averaged in-phase image from said in-phase buffer means (36) for multiplying each pixel of said digital video signal by said multiplier factor and accumulating the result with said in-phase buffer means (36).

10. An assembly as set forth in claim 9 further characterized by said processor means (16) including quadrature channel means for averaging successive frames of said object field (12) 90 degrees out of phase with said reference signal producing an averaged quadrature image frame, and said look-up table including sine multiplier factors corresponding to said phase relationships.

11. An assembly as set forth in claim 10 further characterized by said processor means including quadrature buffer means (40) for storing said averaged quadrature image frame.

12. An assembly as set forth in claim 11 further characterized by said processor means including quadrature imaging means (38) for receiving said multiply command from said correlating means (32) and said digital video signal and said averaged quadrature image frame from said quadrature buffer means (40) for multiplying each pixel of said digital video signal by said sine multiplier factor and accumulating the result with said quadrature buffer means (40).

13. An assembly as set forth in claim 12 further characterized by including stimulus control means (28) for stimulating the object field at said reference signal.

14. An assembly as set forth in claim 13 further characterized by including sensor means (30) for sensing internal periodicity of the object field (12) to produce said reference signal.

15. A method of producing an image synchronous with the periodicity of an object field, the method including the steps of; producing a reference signal representing the periodicity of an object field, detecting radiation from the object field producing a video signal comprising a series of pixels representing a frame of the image of the object field and for producing a timing signal for each of the pixels of the frame, receiving the video signal, storing the frame in synchronism with the reference signal, and averaging the stored frame with subsequently received frames having pixels synchronous with the reference signal producing an image signal, and displaying the averaged image.

16. A method as set forth in claim 15 further including receiving the image signal and converting it into a display signal.

17. A method as set forth in claim 16 further including digitizing the video signal to produce a digital video signal for the storing and averaging.

18. A method as set forth in claim 17 characterized by further including receiving the timing signal and the reference signal to produce synchronizing signals and transmitting multiply and accumulate commands for the storing and averaging prior to the reception of subsequent frames by the storing and averaging.

19. A method as set forth in claim 18 further including storing phase relationship of the timing signal with corresponding cosine multiplier factors, the multiply command including the multiplier factor for each pixel.

20. A method as set forth in claim 19 characterized by further including averaging successive frames of the object field in-phase with the reference signal.

21. A method as set forth in claim 20 characterized by further including storing the averaged in-phase image frame.

22. A method as set forth in claim 21 characterized by further including receiving the multiply command and digital video signal and average in-phase image for multiplying each pixel of the digital video signal by the multiplier factor and accumulating the result with the stored in-phase image frame.

23. A method as set forth in claim 19 characterized by further including averaging successive frames of an object field 90 degrees out of phase with the reference signal for producing an averaged quadrature image frame.

24. A method as set forth in claim 23 characterized by further including storing the averaged quadrature image frame.

25. A method as set forth in claim 24 further characterized by including receiving the multiply command and the digital video signal and the averaged quadrature image frame and multiplying each pixel of the digital video signal by a sinemultiplier factor included within the multiply command and accumulating the result with the averaged quadrature image frame.

26. A method as set forth in claim 25 further including stimulating the object field at the reference signal.

27. A method as set forth in claim 26 further including sensing the internal periodicity of the object field to produce the reference signal.

* * * * *